United States Patent [19]

Osono et al.

[11] 4,039,660
[45] Aug. 2, 1977

[54] ANTIBIOTIC Y-G19Z D3 AND THE PRODUCTION THEREOF

[75] Inventors: Takashi Osono, Tokyo; Shunichi Watanabe, Omiya; Takeshi Saito, Tokyo; Hiroshi Gushima, Ageo; Keisuke Murakami, Wako; Isao Takahashi, Tokyo; Hiroshi Yamaguchi, Omiya; Toshio Sasaki, Tokyo; Yoshihiko Oka, Kawagoe, all of Japan

[73] Assignee: Yamanouchi Pharmaceutical Co., Ltd., Tokyo, Japan

[21] Appl. No.: 613,738

[22] Filed: Sept. 16, 1975

[30] Foreign Application Priority Data

Sept. 24, 1974 Japan ................................ 49-109753

[51] Int. Cl.$^2$ ............................................. A61K 35/74

[52] U.S. Cl. ................................... 424/117; 424/246; 195/80 R

[58] Field of Search ....................... 424/117; 195/80 R

[56] References Cited

U.S. PATENT DOCUMENTS

| | | | |
|---|---|---|---|
| 3,495,003 | 2/1970 | Hausmann et al. | 424/117 |
| 3,639,581 | 2/1972 | Argoudelis et al. | 424/117 |
| 3,761,587 | 9/1973 | Miyairi et al. | 424/117 |

*Primary Examiner*—Jerome D. Goldberg
*Attorney, Agent, or Firm*—Burgess, Ryan and Wayne

[57] ABSTRACT

A new antibiotic substance, designated Y-G19ZD3, is produced by the fermentation of a newly discovered microorganism *Streptomyces organonensis* Y-G19Z or a mutant thereof. The antibiotic substance Y-G19ZD3 is effective against gram negative bacteria and is useful also as an intermediate for the production of other antibiotics.

3 Claims, 2 Drawing Figures

ANTIBIOTIC Y-G19Z D3 AND THE PRODUCTION THEREOF

DETAILED DESCRIPTION OF THE INVENTION

This invention relates to an antibiotic substance Y-G19ZD3. This invention is also concerned with a process for producing the aforesaid antibiotic substance by cultivation of a newly discovered microorganism *Streptomyces oganonensis* Y-G19Z or mutants thereof. The antibiotic substance belongs to the 7-methoxy cephalosporin group. The group of 7-methoxy cephalosporins was recently found to be effective against gram positive and negative bacteria and cephalosporin resistant bacteria.

We have found that the antibiotic substance, Y-G19ZD3, is produced in a cultured broth of *Streptomyces oganonensis* Y-G19Z which was isolated from a soil sample collected at Ogano Town, Chichibu, Saitama Prefecture, Japan.

The physical and chemical properties of antibiotic Y-G19ZD3, which is produced by this invention are given below. These data are concerned with the most purified sample now available, and will be varied when the sample is further purified.

Figure 1:
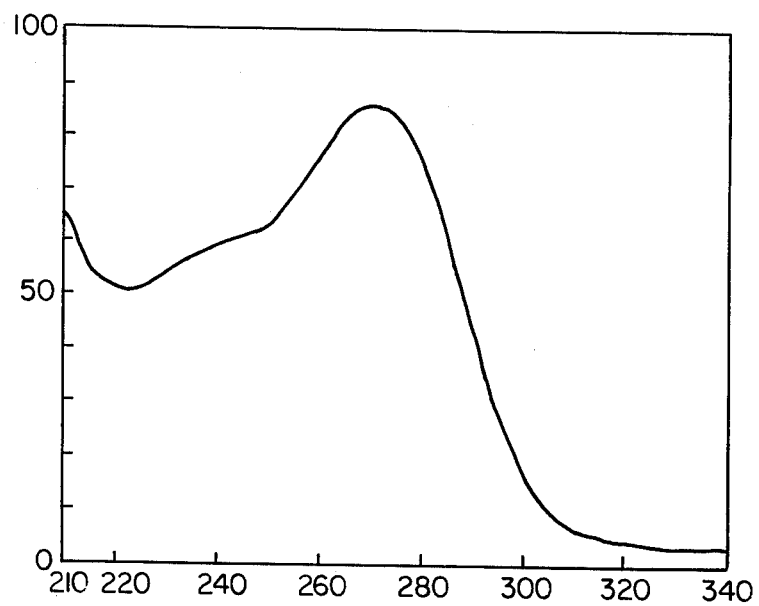
Figure 2:
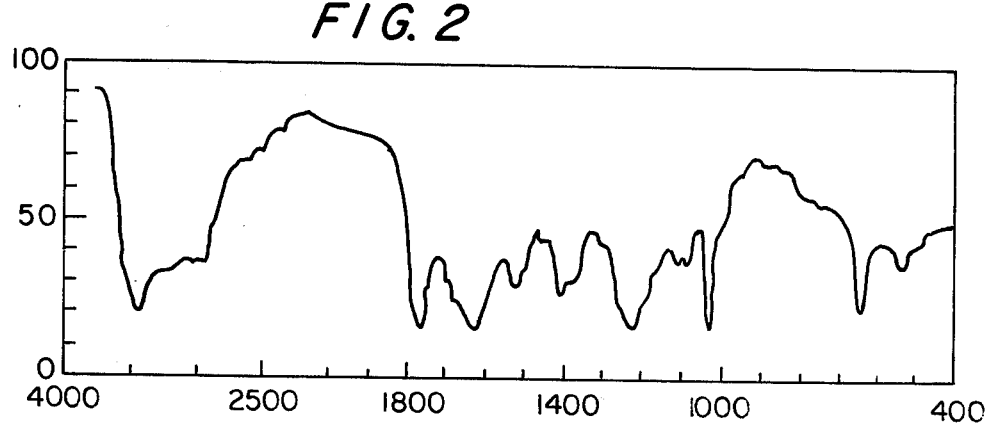

1. Appearance: white powder
2. Melting point: 160°–170 ° C (decomp.)
3. Solubility: easily soluble in water; difficult soluble in methanol and ethanol; almost insoluble in other organic solvents.
4. Elemental analysis: (as sodium salt)
    Found: C 31.8%; H 3.8%; N 7.1%; S 16.5%; Na 7 ± 0.7%.
5. Optical rotation:
    $[\alpha]_D^{20} = + 42°$ (C=1%, in water)
6. High-voltage paper electrophoresis:
    (done on Whatman No. 1 paper at 42 V/cm in 10% acetic acid at pH 2.2).
    The distance moved for 1 hour, Y-19ZD3 −5.2 cm; cysteic acid −6.5 cm; glutathione −0.9 cm; cephalosporin C −2.7 cm; 7-methoxy cephalosprin C −2.8 cm.
7. Color reaction: positive for ninhydrin
8. Nature of substance: amphoteric
9. Hydrolysis product: α-aminoadipic acid by 6 N HCl hydrolysis
10. Ultraviolet absorption spectrum measured in 1/100 M phosphate buffer solution at pH 6.4 (as shown in FIG. 1)
    $\lambda_{max}$: 272 mμ ($E_{1cm}^{1\ percent}$ 176), 243 m μ (shoulder)
11. Infrared absorption spectrum measured in KBr tablet (as shown in FIG. 2)
    absorption maxima: 3420, 1765, 1625, 1520, 1405, 1220, 1030 and 640 cm$^{-1}$.
12. Nuclear magnetic resonance spectrum measured in heavy water solution:
    δ (ppm) 1.80 (4H, multiplet), 2.43 (2H, multiplet); 3.35–3.82 (2H, quartet, J=18Hz); 3,47 (3H, singlet), 3.82 (1H, multiplet); 4.01 (2H, singlet), 5.13 (1H, singlet).
13. Thin layer chromatography (ascending method) using Avicel SF® (manufactured by Pharmacia, Uppsala, Sweden): Rf values are shown in Table 1.

Table 1

| Sample | Developing solvent | | |
|---|---|---|---|
| | I | II | III |
| Y-G19ZD3 | 0.35 | 0.16 | 0.19 |
| Reference substance (A) | 0.32 | 0.27 | 0.33 |
| Reference substance (B) | 0.31 | 0.27 | 0.32 |

| Components | |
|---|---|
| | Volume ratio |
| Developing solvent: | |
| I acetonitrile: water | 5:2 |
| II n-butanol: acetic acid: water | 6:1.5:2.5 |
| III n-butanol: acetic acid: water | 4:1:2 |

Reference substance A:
  7-(5-amino-5-carboxyvaleramido)-7-methoxy cephalosporanic acid.
  [R.Nagarajan et al., cf. J.A.C.S., 93 (9) 2308–2312 (1971)].
Reference substance B:
  7-(5-amino-5-carboxyvaleramido)-3-carbamoyl oxymethyl-7-methoxy-3-cephem-4-carboxylic acid.
  [Belgian Patent No. 764,160; German Offenlegungsshrift No. 2,166,462 and 2,166,463; French Pat. No. 2,085,702; British Pat. No. 1,321,412; Canadian Pat. No. 960,169; Dutch Pat. No. 71.03360].

The results shown above, especially the typical infrared band at 1765 cm$^{-1}$ (cyclic lactam), nuclear magnetic resonance signals at 3.47 ppm (3H, singlet, 7-OCH$_3$) and 5.13 ppm (1H, singlet, 6-CH), indicate that the antibiotic substance Y-G19ZD3 belongs to one of 7-methoxy cephalosporin group antibiotics.

The minimum inhibitory concentrations against various microbes are shown in the following table 2.

Table 2

Minimum inhibitory concentrations of antibiotic Y-G19ZD3
(Agar dilution method using heart infusion agar at pH 7.4)

| Organism | M I C (mcg/ml) |
|---|---|
| *Escherichia coli* Kauffmann 014 1 | 50 |
| *Escherichia coli* NIHJ | 50 |
| *Klebsiella pneumoniae* ATCC 10031 | 6.25 |
| *Salmonella cholerae-suis* 1348 | 6.25 |
| *Salmonella typhi* H901W | 6.25 |
| *Salmonella enteritidis* 1891 | 6.25 |
| *Shigella flexneri* 2a 1675 | 50 |
| *Shigella sonnei* II 37148 | 100 |
| *Proteus vulgaris* OXK US | 3.13 |
| *Proteus mirabilis* IFM OM–9 | 12.5 |
| *Pseudomonas aeruginosa* ATCC 8689 | >100 |
| *Pseudomonas ovalis* IAM 1002 | >100 |
| *Pseudomonas melanogenum* IAM 1655 | >100 |
| *Bacillus megatherium* 10778 | >100 |
| *Bacillus subtilis* ATCc 6633 | >100 |
| *Micrococcus flavus* ATCC 10240 | >100 |
| *Sarcina lutea* ATCC 9341 | >100 |
| *Staphylococcus aureus* 209P | >100 |
| *Staphylococcus aureus* Smith | >100 |
| *Staphylococcus aureus* Terashima | >100 |
| *Corynebacterium xerosis* | >100 |
| Mycobacterium 607 | >100 |
| *Mycobacterium phlei* | >100 |

Antimicrobial activities of Y-G19ZD3 in comparison with those of Cephalosporin C against various microorganisms are shown in Table 3. The figure indicates the diameter (mm) of the inhibition zone obtained with a disc dipped in 125 mcg/ml solution on Heart infusion agar seeded with each organism.

Table 3

| Organism | Y-G19ZD3 | Cephalosporin C |
|---|---|---|
| *Basillus subtilis* ATCC 6633 | 0 | 13.5 |
| *Staphylococcus aureus* 209 P | 0 | 0 |
| *Sarcina lutea* ATCC 9941 | 0 | 0 |
| *Klebsiella pneumoniae* | 14.2 | 0 |
| *Escherichia coli* NIHJ | 15.4 | ± |
| *Proteus mirabilis* IMF-OM9 | 15.7 | 17.6 |
| *Proteus vulgaris* | 15.0 | 0 |
| *Proteus morganii* | 0 | 0 |

As is apparent from the tables 2 and 3, Y-G19Z D3 shows high antibacterial activities against gram negative bacteria. Thus, the antibiotic substance Y-G19 ZD3 will be effective for the treatment of diseases caused by gram negative bacteria and will be useful also as an intermediate for production of other semi-synthetic antibiotics.

Characteristics of the above antibiotic Y-G19ZD3 producing microorganism, *Streptomyces oganonensis* Y-G19Z are as follows:

I. Morphological characteristics of *S. oganonensis* Y-G19Z

It grows both on natural and synthetic media with formation of well branched substrate mycelium, while formation of aerial mycelium is not sufficient and hence the formation of spores is poor. Spore chains are straight, belong to R (Rectus) or RF (Rectiflexibiles) type and bear 10-50 spores on each chain. Spores are elliptical, spherical or cylindrical in shape and $0.45-0.60 \times 0.55-0.90 \mu$ in size. Spore surface is smooth. Neither flagellate spore nor sporangium was observed.

III. Physiological properties of *S. oganonensis* Y-G19Z

| | |
|---|---|
| Tyrosinase formation | negative |
| Nitrate reduction | positive |
| Skim milk coagulation | positive, weakly |
| Skim milk peptonization | positive, weakly |
| Hydrolysis of starch | positive |
| Liquefaction of gelatin | positive, weakly |
| Cellulose decomposition | negative |
| Hemolysis | positive |
| Solubilization of calcium malate | positive |

Utilization of carbon compounds by *S. oganonensis* Y-G19Z

| Carbon source | Utilization |
|---|---|
| Glucose | + |
| Arabinose | + |
| Sucrose | − |
| Xylose | + |
| Inositol | − |
| Mannitol | + |
| Fructose | + |
| Rhamnose | − |
| Raffinose | − |

Characteristic features of *Streptomyces oganonensis* Y-G19Z are summarized as follows:
1. It belongs to non-chromogenic Streptmyces strain.
2. Its aerial mycelium is straight without verticils (R or RF type).
3. Spores are spherical or elliptical.
4. Spore surface is smooth.
5. It gives pale yellowish gray to pale yellowish brown growth on various media.
6. Color of aerial mycelium is brownish white, yellowish white and yellowish gray.
7. Antibiotic substance Y-G19ZD3 belonging to 7-methoxy cephalosporin group is produced.

On searching known strains having the above properties, the following species may be mentioned as the most II. Cultural Characteristics *S. oganonensis* Y-G19Z

| Medium | Growth | Aerial mycelium | Soluble pigment |
|---|---|---|---|
| Czapek's agar | very poor, white | scant white | none |
| Glucose Czapek's agar | good, cream yellow | fair, yellowish gray | very slightly |
| Glucose asparagine agar | good, white | poor, white | none |
| Glycerol asparagine agar | good, white to yellowish white | poor white to yellowish white | none |
| Inorganic salt starch agar | good, yellowish gray to pale yellowish brown | poor, yellowish gray | none |
| Tyrosine agar | good, pale yellow | poor, yellowish gray | slightly, pale yellowish gray |
| Medium | Growth | Aerial mycelium | Soluble pigment |
| Iron and yeast extract tyrosine agar | good, pale yellow to yellowish brown | good, brownish white to yellowish gray | very slightly light brownish gray |
| Nutrient agar | good, pale yellowish brown | good, powdery pale orange to pale brown | slightly, yellowish brown |
| Bennett's agar | good, pale yellowish brown | good, brownish gray, pale orange to pale pink | very slightly |
| Calcium malate agar | moderate cream | none | none |
| Potato plug | good, pale yellowish brown | good, yellowish gray to pale brownish gray | brownish gray to dark yellowish brown |
| Blood agar | good, olive gray to dark olive gray | none | yellowish gray to dark reddish brown |
| Loffler's serum medium | good | none | none | closely related strains. *Streptomyces globisporus*, described in S.A. Waksman: the Actinomycetes 2, 218 (1961) and International Journal of Systematic Bacteriology, 18, (4) 324–325 (1968).

However, when compared with *S. globisporus* disclosed in the above literatures, strain Y-G19Z differs from it in the following points shown in the table.

Table

| Characteristic | Y-G19Z | S. globisporus |
| --- | --- | --- |
| Size of spore (μ) | 0.45–0.60 × 0.55–0.90 | 1.2–1.4 × 1.8–2.0 or 0.9–1.4 spherical |
| Soluble pigment or glycerol asparagine medium | none | yellow to greenish yellow |
| Rhamnose utilization | negative | positive |
| Starch hydrolysis | strong | weak |
| Skim milk coagulation | positive | negative |
| Skim milk peptonization | weak | strong |
| Production of cephalosporin antibiotics | positive | negative |

From the above differences, the strain Y-G19Z was identified as a new species distinctly different from *Streptomyces globisporus* and named *Streptomyces oganonensis* Y-G19Z. The strain Y-G19Z has been placed on permanent deposit without restriction as to availability under an accession No. FERM-P 2725 in Technical Research Institute of Microbial Industry, Agency of Industrial Science & Technology, Ministry of International Trade and Industry, Japan, and also as ATCC 31167 in American Type Culture Collection, 12301 Parklawn Drive, Rockville Md. 20852.

All restrictions on the availability of the culture deposit to the public will be irrevocably removed on the granting of the patent and the culture will be maintained by the depositor throughout the effective life of the patent.

Although we have explained the characteristics of strain Y-G19Z in the foregoing, it is well-known that various properties of Streptomyces are changeable, and may easily be varied naturally and artificially. Thus the strains which may be employed in this invention include all of the strains which belong to the genus of Streptomyces and are capable of producing antibiotic Y-G19ZD3. Further the productivity of Y-G19ZD3 by the strain used in this invention may be raised by treatment with X-ray or UV-light iradiation, chemical mutagens, radiomimetic agent, and by transformation, transduction, recombination, and other genetic methods useful for obtaining mutants.

The production of Y-G19ZD3 is carried out by cultivation of *Streptomyces oganonensis* Y-G19Z or other Y-G19ZD3-producing strains belonging to Streptomyces in various culture media.

Cultivation in the process of this invention may be carried out according to the method generally employed for microorganism, but submerged culture in liquid media is preferable.

As the medium for cultivation, can be used any medium which contains nutrients Y-G19ZD3-producing strains belonging Streptomyces can utilize: that is, synthetic, semi-synthetic or natural medium containing, as assimilable carbon sources, for example, glucose, mannitol, glycerol, dextrin, starch, vegetable oil, etc., and as assimilable nitrogen sources, meat extract, peptone, gluten meal, cotton seed meal, soybean meal, peanut meal, fish meal, corn steep liquor, dried yeast, yeast extract, ammonium sulfate, ammonium nitrate, urea and other organic or inorganic nitrogen sources. Metal salts such as sulfate, nitrate, chloride, carbonate, phosphate of sodium, potassium, magnesium, calcium, zinc, iron, etc., may also be added, when necessary.

Furthermore, methionine, cysteine, cystine, thiosulfate, methyl oleate, lard, silicon oil, surfactants, etc., may be added as accelerators of antibiotic production or antifoam agents.

The cultivation may be carried out advantageously under aerobic condition and the temperature may be usually at 18°–35° C, preferably about 30° C and the pH of the medium may be at 5–10, preferably at pH 6–8. Cultivation period varies according to the composition of medium, cultivation temperature, etc. Usually the period is 3–10 days and the antibiotic substance Y-G19ZD3 is accumulated in the culture medium.

The separation and purification of the antibiotic substance Y-G19ZD3 is carried out by any one or combination of conventional methods used for separation and purification of antibiotics from culture media.

The antibiotic substance Y-G19ZD3 is soluble in water, thus after completion of cultivation, mycelium and other solid mass are removed by centrifugation or filtration, and Y-G19ZD3 contained in supernatant or filtrate may be separated by any one or combination of the conventional methods utilizing its physico-chemical properties such as difference in solubilities in solvents, difference in tendencies to separate out from solutions and to adsorb onto adsorbents, distribution coefficient between two immiscible solvents and others. These methods may be applied singly or in combination in voluntary order or repeatedly.

The process of this invention is more illustratively explained by the following examples, but the production according to this invention may be practised in various manners based on the properties of Y-G19ZD3 as disclosed above.

Thus, this invention is not limited to the examples hereunder described but includes all the methods for production, separation and purification of Y-G19ZD3 by wellknown means based upon the above-proved properties of Y-G19ZD3 through this invention using Y-G19Z strain or mutants thereof or Y-G19ZD3-producing strains which belong to the genus Streptomyces.

EXAMPLE 1

Inoculum preparation:

Sakaguchi flask inoculum of Streptomyces oganonensis Y-G19Z was prepared by inoculating 100 ml of nutrient medium placed in 500 ml flask, sterilized at 120° C for 20 minutes, with seed from an agar slant culture.

The following medium is ordinarily used.

| | |
| --- | --- |
| Starch | 10 g |
| Glucose | 10 g |
| Soy bean meal | 15 g |
| Yeast extract | 5 g |
| Water | to 1000 ml |

The flasks were incubated at 30° C for 48 hours on a rotary shaker. A forty to sixty ml portion of the culture thus obtained was inoculated into a 400 ml batch of the same medium in 2000 ml Sakaguchi flask and was incubated at 30° C for 24 hours.

Fermentation

For the production of antibiotic Y-G19ZD3 the following fermentation medium was preferably used (main medium).

| | |
|---|---|
| Starch | 45 g |
| Glycerol | 7.5 g |
| Corn steep liquor | 1 g |
| Gluten meal | 1 g |
| Soy bean meal | 25 g |
| Casein hydrolysate | 3 g |
| Ferrous sulfate | 0.1 g |
| Water to | 1000 ml |
| Adekanol®* | 10 ml |

*Antifoam agent available from Asahi Denka Kogyo Co.

A 60 liter batch of the main medium was placed in a 100 liter fermenter, and sterilized at 120° C for 30 minutes. A 800 ml portion of the above-prepared inoculum culture was inoculated in the sterile main medium. The fermentation was maintained at 30° C and was continued for 90 hours, at which time the broth was harvested.

Purification Procedure:

The cultured broths from two 100 liter fermenters were combined and adjusted to pH 3.0 with dilute hydrochloric acid. Radiolite No. 900 (Showa Chemical Industry Co., Ltd.) was added to the combined broth which was stirred and was filtered through a filter press whereupon about 100 liter of filtrate was obtained. The filtrate was re-adjusted to pH 3.0 and was passed through a column packed with 10 liter of Amberlite XAD-2 (available from Rohm & Haas Co.). The effluent was adjusted to pH 5.0 by sodium hydroxide and stirred for 2 hours after addition of 3.0 Kg of active charcoal, whereupon the antibiotic Y-G19ZD3 was adsorbed. Cake of the active charcoal obtained by filtration was extracted with about 60 liter of 50 V/V % aqueous acetone. The extract was concentrated to about 30 liter under reduced pressure, adjusted to pH 2.5 with dilute hydrochloric acid, and passed through a column packed with 5 liter of ion exchanger, Duolite A-6 ($CH_3COO^-$ type) (available from Chemical Process Co.). The column was washed with water and the antibiotic was eluted with about 50 liter of a mixture of pyridine:acetic acid: water (volume ratio; 100: 7: 900, pH 6.0). The eluate was concentrated to 2-3 liter under reduced pressure and was passed through a column packed with 2 liters of Amberlite CG-50 ($H^+$ type) (available from Rohm & Haas Co.). The active fraction obtained was adjusted to pH 3.0 and washed with an equal volume of n-butanol. The aqueous layer was adjusted to pH 4.0 and concentrated to 500-1000 ml, to which 250-500 ml of methanol and 10-20 liters of acetone were added successively whereupon a glutinous precipitate was formed. The precipitate was collected and dissolved in water and the aqueous solution was adjusted to pH 4.0 and lyophilized to give crude powder weighing about 200 g.

One hundred grams of the crude powder was dissolved in 50 to 100 ml of 0.5 M ammonium bromide-acetic acid mixture (pH 3.0). The solution obtained was fractionated by passing through a column packed with 1.5 liter of DEAE Sephadex A 25 (available from Pharmacia, Uppsala, Sweden) which was pre-equilibrated with 0.5 M ammonium bromide-acetic acid mixture (pH 3.0). The antimicrobially active fractions were combined and diluted with 5-10 volumes of water, and adjusted to pH 2.5 with dilute hydrochloric acid. The active fraction was re-passed through a column packed with Duolite A-6 ($CH_3COO^-$ type) for adsorption thereon. The column was thoroughly washed with water and was eluted with the mixture of pyridine:acetic acid:water (volume ratio 100: 7 : 900). The antimicrobially active fractions were collected and re-treated with a column packed with Amberlite CG-50 ($H^+$ type). Then the active fractions obtained were concentrated and 10 volumes of ethanol and 10 volumes of acetone were added successively to give about 5 g of pale yellow powder. The powder was dissolved in a small amount of a mixture of isopropanol:methanol:water (volume ratio 5: 6 : 5) and chromatographed with a column packed with micro crystalline cellulose (Avicel, availabe from American Viscose Co.) which was pre-equilibrated with the same solvent mixture.

The antimicrobially active and ninhydrin-positive fractions were collected, combined, concentrated and 50-100 volumes of ethanol were added to precipitate the active substance as a pale-yellow powder.

The active powder was dissolved in a small amount of a mixture of n-butanol:acetic acid:water (volume ratio 4: 1 : 2) and chromatographed with a column packed with micro crystalline cellulose which was pre-equilibrated with the same solvent mixture. Fractions which gave an Rf of 0.19 by a thin layer chromatography on a cellulose plate (Avicel SF plate, available from American Viscose Co.) developed with the same solvent mixture and visualized by spraying 0.25 % ninhydrin solution in pyridine followed by heating, were collected and concentrated, to which ethanol was added to give 80 mg of a white powder of antibiotic Y-G19ZD3, free acid.

EXAMPLE 2

Free acid of antibiotic Y-G19Z D3 obtained in Example 1 was dissolved in a small amount of water, and was fractionated by a chromatography using Dowex 50 W ($H^+$ type) (available from Dow Chemical Co.) which was developed with water. Microbiologically active fractions were collected and concentrated at 40° to 45° C under reduced pressure. The concentrate was adjusted to pH 7.0 with sodium hydroxide, and was lyophilized. The dried powder obtained was chromatographed with a column packed with microcrystalline cellulose (Avicel, available from American Viscose Co.) which was pre-equilibrated and developed with a solvent mixture of isopropanol : water (volume ratio 7 : 3). Active fractions giving an Rf of 0.19 on a cellulose thin layer chromatogram described in Example 1 were collected and concentrated to dryness. A powder obtained was dissolved in a small amount of water and a large quantity of ethanol was thereto added to yield a white precipitate, which gave, after drying, sodium salt of antibiotic Y-G19Z D3.

EXAMPLE 3

In a 100 liter fermenter was placed 60 liter of a culture medium having a composition of 5.0% soybean meal, 7.0% starch, 0.8% glycerol, 0.1% casein hydrolysate, 0.5% sodium thiosulfate and less than 1% Adekanol, and was sterilized at 120° C for 30 minutes. A 800 ml portion of the inoculum culture prepared according to Example 1 was seeded in the above sterile medium. The fermentation was continued at 30° C under agitation for 96 hours. Havested broth was filtered as described in Example 1, and the filtrate was passed through a column packed with 5 liter of Amberlite XAD-2. Effluent from the column was further passed through a column packed with 5 liters of ion exchanger Dowex 1 × 2 ($Cl^-$ type) (available from Dow Chemical Co.), which was washed thoroughly with water and thereafter was eluted with 25 liters of 5% sodium chloride solution. To the eluate was added 2% (w/v) of active charcoal to which the antibiotic was adsorbed. Cake of active charcoal was washed with water and eluted with 50% aqueous acetone. The eluate was concentrated and lyophilized to give 27.9 g of crude powder which contained 5.6 g of active substance.

The lyophilized crude powder was processed as described in Example 1, and 510 mg of antibiotic Y-G19Z D3 free acid was obtained.

What is claimed is:

1. The antibiotic Y-G19Z D3, a compound of 7-methoxy cephalosporin group, or pharmaceutically acceptable salts thereof, which in its most purified state
   a. is a white amorphous powder of amphoteric nature
   b. has melting point of 160°–170° C (decomposition)
   c. is easily soluble in water
   d. is difficultly soluble in methanol and ethanol
   e. is almost insoluble in other organic solvents
   f. has an elemental composition (percent) (as sodium salt)
      C: 31.8 H: 3.8 N: 7.1 S: 16.5 Na: 7 ± 0.7
   g. has the following value in high voltage paper electrophoresis on Whatman No. 1 paper in 10% acetic acid at pH 2.2:
      The distance moved at 42 V/cm during 1 hour −5.2 cm
   h. give α-aminoadipic acid by acidic hydrolysis
   i. in 1/100 M phosphate buffer solution at pH 6.4 has characteristic ultraviolet absorption spectrum as shown FIG. 1 of the drawing:
      $\lambda_{max}$ 272 mμ ( $E_{1cm}^{1\%}$ 176 ), 243 mμ (shoulder)
   j. in KBr tablet has a chracteristic infrared absorption spectrum as shown in FIG. 2 of the drawing
   k. in heavy water has a chracteristic nuclear magnetic resonance spectrum as follows:
      β value (ppm): 1.80 (4H, multiplet), 2.43 (2H, multiplet) 3.35 – 3.82 (2H, quartet, J=18Hz), 3.47 (3H, singlet), 3.82 (1H, multiplet) 4.01 (2H, singlet), 5.13 (1H, singlet)
   l. has the following Rf values in thin layer chromatography using microcrystalline cellulose systems indicated as below

| Solvent system (volume ratio) | Rf value |
| --- | --- |
| Acetonitrile : H$_2$O (5 : 2) | 0.35 |
| n-Butanol : Acetic acid : H$_2$O (6 : 1.5 : 2.5) | 0.16 |
| n-Butanol : Acetic acid : H$_2$O (4 : 1 : 2) | 0.19 |

2. The sodium salt of the antibiotic Y-G19Z D3, as set out in claim 1.

3. The method for producing antibiotic Y-G19Z D3 as defined in claim 1 which comprises cultivating Streptomyces oganonensis Y-G19Z ATCC-31167 in a culture medium containing assimilable sources of carbohydrate, nitrogen and inorganic salts under submerged aerobic fermentation conditions until a substantial amount of antibiotic activity is produced by said organism in said culture medium, and separating and recovering the Y-G19Z D3 antibiotic mixture from said culture medium.